United States Patent
Namiki et al.

(12)

(10) Patent No.: US 7,531,576 B2
(45) Date of Patent: May 12, 2009

(54) BIPHENYL DERIVATIVES

(75) Inventors: Takayuki Namiki, Yokohama (JP); Kenichi Kishii, Yokohama (JP); Masaki Mitani, Yokohama (JP); Masashi Tamai, Yokohama (JP); Naoki Hiyama, Yokohama (JP); Makoto Kimura, Yokohama (JP); Satoshi Ichinomiya, Yokohama (JP)

(73) Assignee: Pola Chemical Industries, Inc., Shizuoka-shi (JP)

( * ) Notice: Subject to any disclaimer, the term of this patent is extended or adjusted under 35 U.S.C. 154(b) by 473 days.

(21) Appl. No.: 10/451,408

(22) PCT Filed: Dec. 5, 2001

(86) PCT No.: PCT/JP01/10626

§ 371 (c)(1),
(2), (4) Date: Jun. 23, 2003

(87) PCT Pub. No.: WO02/051799

PCT Pub. Date: Jul. 4, 2002

(65) Prior Publication Data

US 2004/0048909 A1  Mar. 11, 2004

(30) Foreign Application Priority Data

Dec. 26, 2000  (JP)  ................ 2000-394372

(51) Int. Cl.
| | |
|---|---|
| *A01N 47/28* | (2006.01) |
| *A01N 41/02* | (2006.01) |
| *A01N 41/06* | (2006.01) |
| *A01N 37/18* | (2006.01) |
| *C07C 273/00* | (2006.01) |
| *C07C 333/00* | (2006.01) |
| *C07C 303/00* | (2006.01) |
| *C07C 233/00* | (2006.01) |

(52) U.S. Cl. .............. 514/595; 514/600; 514/602; 514/617; 564/56; 564/79; 564/80; 564/123

(58) Field of Classification Search .............. 514/381, 514/595, 600, 602, 617; 564/56, 79, 80, 564/123
See application file for complete search history.

(56) References Cited

U.S. PATENT DOCUMENTS

| | | | | |
|---|---|---|---|---|
| 4,985,440 A | * | 1/1991 | Cozzi et al. ............ | 514/397 |
| 5,006,546 A | * | 4/1991 | Coffee ............ | 514/397 |
| 5,143,919 A | * | 9/1992 | Meguro et al. ............ | 514/291 |
| 5,312,820 A | * | 5/1994 | Ashton et al. ............ | 514/227.5 |
| 5,362,878 A | * | 11/1994 | Chang et al. ............ | 546/296 |
| 5,397,781 A | * | 3/1995 | Yanagibashi et al. ............ | 514/256 |
| 5,399,578 A | | 3/1995 | Bühlmayer et al. | |
| 5,965,592 A | | 10/1999 | Bühlmayer et al. | |
| 6,969,711 B2 | * | 11/2005 | Shibuya et al. ............ | 514/218 |

FOREIGN PATENT DOCUMENTS

| | | |
|---|---|---|
| EP | 0 433 662 | 6/1991 |
| JP | 6-211814 | 8/1994 |
| JP | 06211814 | * 8/1994 |
| JP | 7-48360 | 2/1995 |
| JP | 07048360 | * 2/1995 |
| WO | WO 93/04052 | 3/1993 |
| WO | WO 96/10559 | 4/1996 |
| WO | 99/12534 | 3/1999 |
| WO | WO-9912534 | * 3/1999 |

OTHER PUBLICATIONS

DialogWeb Command Mode, 0005644522, English translation of the abstract of JP 04-235149, pp. 1-3 (2007) (corresponds to US Patents 5,399,578 and 5,965,592).

* cited by examiner

*Primary Examiner*—Alton N Pryor
(74) *Attorney, Agent, or Firm*—Oblon, Spivak, McClelland, Maier & Neustadt, P.C.

(57) ABSTRACT

Biphenyl derivatives represented by the following formula (1):

wherein $R^1$ represents a $C_{5-7}$ alkyl group, $R^2$ represents a substituted or unsubstituted aromatic hydrocarbon, or cycloalkyl group, $R^3$ represents a tetrazolyl group, —NHCOCF$_3$, —NHSO$_2$CF$_3$ or —SO$_2$NHCONHR$^4$ in which $R^4$ represents a substituted or unsubstituted aromatic hydrocarbon group, and Z represents a single bond, a $C_{1-4}$ alkylene group or —SO$_2$NH—, and salts thereof; and ACAT inhibitors and medicines containing them as active ingredients.

The compounds according to the present invention possess excellent ACAT inhibitory activities, and are useful as preventives and/or therapeutics for diseases cased by the enhancement of ACAT activity, for example, hypercholesterolemia, atherosclerosis and the like.

9 Claims, No Drawings

BIPHENYL DERIVATIVES

TECHNICAL FIELD

This invention relates to compounds possessing excellent acyl-CoA:cholesterol acyltransferase (hereinafter abbreviated as "ACAT") inhibitory activities, and also to medicines containing the same.

BACKGROUND ART

Free cholesterol has important physiological activities as a constituent of cell membranes and the precursor of bile acids, and also as a regulatory factor for the metabolism of cholesterol. In hyperlipidemia characterized by an extraordinarily high value of serum cholesterol or the like, however, it has been considered that atherosclerosis advances to result in an increase of the onset risk of coronary diseases. An increase of serum cholesterol has been, therefore, ranked as the greatest risk factor for coronary diseases.

ACAT is an enzyme which catalyzes esterification of cholesterol in cells, and physiologically, plays an important role in the control of the free cholesterol levels in blood and cells. It has been reported that the physiological role of ACAT differs depending on the tissue and that ACAT takes part in the absorption of exogenous cholesterol in the small intestine, in the secretion of very-low-density lipoproteins (VLDL) in the liver, and in the accumulation of cholesterol esters in arterial walls. However, the enhanced ACAT activity leads to an onset and advancement of hyperlipidemia and arteriosclerosis due to the increase of serum lipids and the formation of foam cells based on the excessive accumulation of cholesterol esters in arterial walls.

The inhibition of ACAT activity is, therefore, expected to bring about lipid lowering effect on the basis of the suppression of cholesterol absorption through the digestive tracts and the suppression of VLDL secretion from the liver, and further, antiarteriosclerotic effect on the basis of the suppression of the formation of foam cells. Aiming at hyperlipidemia treatment agents and antiarteriosclerotic agents, a variety of substances having ACAT inhibitory activity has been developed accordingly. Under the current circumstances, however, these conventional ACAT inhibitors have not found practical utility yet, because, in clinical trials, they have not been able to obtain sufficient effect or have induced side effects such as hepatopathy, degeneration or necrosis of the adrenal cortex, and diarrhea caused by the suppression of fat absorption.

An object of the present invention is, therefore, to provide a new substance having ACAT inhibitory activity and a medicine containing the same.

DISCLOSURE OF THE INVENTION

With the foregoing circumstances in view, the present inventors have proceeded with an extensive investigation. As a result, it has been found that the compounds represented by the formula (1) described below and salts thereof have excellent ACAT inhibitory activities and are useful as preventives and/or therapeutics for diseases caused by the enhancement of ACAT activity, for example, hypercholesterolemia, atherosclerosis and the like, leading to the completion of the present invention.

Specifically, the present invention provides a biphenyl derivative represented by the following formula (1):

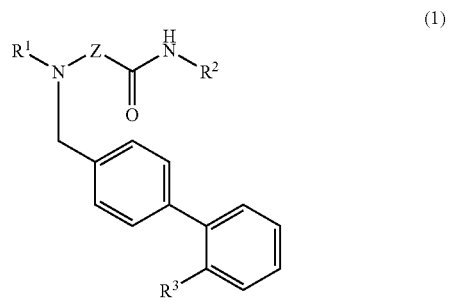

wherein $R^1$ represents a $C_{5-7}$ alkyl group, $R^2$ represents a substituted or unsubstituted aromatic hydrocarbon, or a cycloalkyl group, $R^3$ represents a tetrazolyl group, —NHCOCF$_3$, —NHSO$_2$CF$_3$ or —SO$_2$NHCONHR$^4$ in which $R^4$ represents a substituted or unsubstituted aromatic hydrocarbon group, and Z represents a single bond, a $C_{1-4}$ alkylene group or —SO$_2$NH—, or a salt thereof; and an ACAT inhibitor and medicine containing them as an active ingredient.

The present invention also provides a medicinal composition comprising the biphenyl derivative or the salt thereof and a pharmacologically acceptable carrier.

The present invention further provides a method for the treatment of a disease caused by the enhancement of ACAT activity, which comprises administering the biphenyl derivative or the salt thereof.

The present invention still further provides use of the biphenyl derivative or the salt thereof for the production of a medicine.

BEST MODES FOR CARRYING OUT THE INVENTION

In the formula (1), the $C_{5-7}$ alkyl group represented by $R^1$ can be either linear or branched, although a linear alkyl group is preferred. Particularly preferred are n-pentyl, n-hexyl and n-heptyl from the standpoint of ACAT inhibitory activity.

As the aromatic hydrocarbons represented by $R^2$ and $R^4$, $C_{6-10}$ aromatic hydrocarbon groups are preferred, with phenyl and naphthyl being more preferred and phenyl being particularly preferred. As the substituents which can substitute on the aromatic hydrocarbon groups, 1 to 3 substituents selected from halogen atoms and $C_{1-5}$ alkyl groups are preferred. Examples of the halogen atoms can include fluorine atom, chlorine atom, bromine atom and iodine atom, with fluorine atom being particularly preferred. The $C_{1-5}$ alkyl groups can be either linear or branched, and their specific examples can include methyl, ethyl, n-propyl, isopropyl, n-butyl, isobutyl, sec-butyl, tert-butyl, n-pentyl and isopentyl. Among these, methyl, ethyl and isopropyl are particularly preferred.

As the cycloalkyl group represented by $R^2$, $C_{3-8}$, especially $C_{5-7}$ cycloalkyl groups are preferred. Specifically, cyclohexyl is particularly preferred.

Preferred as $R^2$ are $C_{6-10}$ aromatic hydrocarbon which may be substituted by 1 to 3 substituents selected from halogen atoms and $C_{1-5}$ alkyl groups, or $C_{3-8}$ cycloalkyl groups, and more preferred are phenyl which may be substituted by 1 to 3 substituents selected from halogen atoms and $C_{1-5}$ alkyl groups, or $C_{5-7}$ cycloalkyl groups. Of these, particularly preferred specific examples of $R^2$ can include di- or trihalogenophenyl groups such as difluorophenyl and trifluorophenyl; di- or tri-$C_{1-5}$ alkylphenyl groups such as diisopropylphenyl and trimethylphenyl; and cyclohexyl.

Preferred as $R^4$ are $C_{6-10}$ aromatic hydrocarbon groups which may be substituted by 1 to 3 substituents selected from halogen atoms and $C_{1-5}$ alkyl groups, and more preferred is a phenyl group which may be substituted by 1 to 3 substituents selected from halogen atoms and $C_{1-5}$ alkyl groups. Of these, particularly preferred specific examples of $R^4$ can include di- or trihalogenophenyl groups such as difluorophenyl and trifluorophenyl; and di- or tri-$C_{1-5}$ alkylphenyl groups such as diisopropylphenyl and trimethylphenyl.

As the tetrazolyl group represented by $R^3$, 5-tetrazolyl is particularly preferred. Particularly preferred examples of $R^3$ can include tetrazolyl, —NHCOCF$_3$ and —NHSO$_2$CF$_3$.

Illustrative of the $C_{1-4}$ alkylene group represented by Z are methylene, ethylene, 1-methylethylene, trimethylene, and tetramethylene, with methylene being particularly preferred. Particularly preferred examples of Z can include a single bond, methylene and —SO$_2$NH—.

No particular limitation is imposed on the salt of the biphenyl derivative represented by the formula (1) [the invention compound (1)], provided that it is physiologically acceptable. Preferred examples, however, can include mineral acid salts such as the hydrochloride, sulfate, phosphate and nitrate; organic acid salts such as the citrate, oxalate, fumarate, maleate, formate, acetate, methanesulfonate, benzenesulfonate and paratoluenesulfonate; the carbonate; alkali metal salts such as the sodium and potassium salts; alkaline earth salts such as the calcium and magnesium salts; and the ammonium salt.

In the present invention, the invention compound (1) or its salt includes its internal salts, adducts, complexes, solvates, hydrates and the like.

The invention compound (1) or its salt can be produced, for example, in accordance with the following reaction scheme:

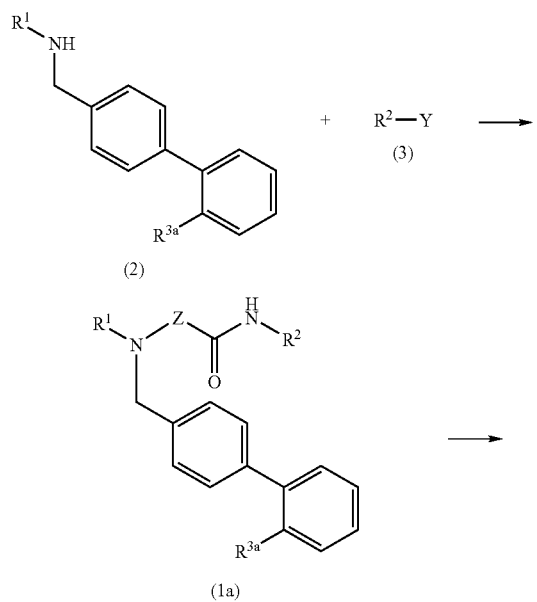

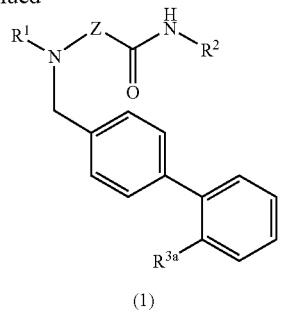

wherein $R^{3a}$ represents a group, which can be converted into $R^3$, or $R^3$ itself; Y represents —NHCOOR$^5$, —NCO, —NHCOCH$_2$X$^1$ or —NHCONHSO$_2$X$^2$ in which $R^5$ represents an alkyl or phenyl group and $X^1$ and $X^2$ represent halogen atoms; and $R^1$, $R^2$ and Z have the same meanings as defined above.

Namely, the invention compound (1) can be obtained by reacting the compound (3) with the secondary amine (2) to obtain the compound (1a) and then converting $R^{3a}$ into $R^3$ as needed.

The secondary amine (2) can be obtained, for example, by condensing an alkylamine with a substituted biphenyl methylhalide. As an alternative, it can also be obtained by reducing an N-alkanoyl-N-substituted biphenyl methylamine, which has been obtained by a reaction between a substituted biphenyl methylamine and a fatty acid halide, with a reducing agent such as lithium aluminum hydride.

As the compound (3), on the other hand, the group described above can be mentioned. For a specific description, use of a carbamate (R$^2$NHCOOR$^5$) or isocyanate (R$^2$NCO) as the compound (3) affords a compound in which Z is a single bond, use of R$^2$—NHCOCH$_2$X$^1$ as the compound (3) yields a compound in which Z is a methylene group, and use of R$^2$—NHCONHSO$_2$X$^2$ as the compound (3) provides a compound in which Z is —SO$_2$NH—.

The condensation reaction between the secondary amine (2) and the compound (3) can be conducted, for example, in the presence of a base such as a tertiary amine or potassium carbonate, although the reaction conditions vary depending on the kind of Y in the compound (3).

As $R^{3a}$, N-protected tetrazolyl groups, nitro group and the like can be mentioned in addition to $R^3$. As an illustrative N-protected tetrazolyl group, N-triphenylmethyltetrazolyl can be mentioned. The deprotection reaction of the protecting group can be conducted preferably by treatment with an acid such as hydrochloric acid. If $R^{3a}$ is a nitro group, a compound in which $R^3$ is —NHCOCF$_3$ or —NHSO$_2$CF$_3$ can be obtained when, after conversion of the nitro group into an amino group by reduction, the amino group is trifluoroacetylated or trifluoromethylsulfonylated.

It is to be noted that the production of the invention compound (1) is not limited to the reaction scheme relying upon the reaction between the secondary amine (2) and the compound (3). As any reaction scheme can be employed insofar as a biphenylmethyl group, $R^1$ and —ZCONHR$^2$ can bind together via a nitrogen atom, it is possible to introduce the biphenylmethyl group or $R^1$ into the nitrogen atom at last.

The salt of the invention compound (1) can be produced, for example, by mixing the invention compound (1) with an acid or base in a polar solvent and/or a non-polar solvent.

The invention compound (1) or the salt thereof, which has been obtained as described above, shows excellent ACAT inhibitory activity and hence, is useful as an ACAT activity inhibitor.

As an ACAT activity inhibitor can reduce the absorption of cholesterol from food, can suppress the secretion of VLDL from the liver and can decrease the accumulation of intracellular cholesterol esters in the walls of blood vessels such as arteries, it can lower the cholesterol level in blood and further, can prevent the formation of lesion parts due to atherosclerosis or the like. Accordingly, the invention compound (1) or its salt is effective for diseases caused by the enhancement of ACAT activity, for example, hypercholesterolemia, atherosclerosis, and various diseases caused by such diseases in mammals (for example, men, mice, rats, rabbits, dogs, monkeys, and the like), and is effective as preventives and/or therapeutics for such diseases. Incidentally, specific examples of hypercholesterolemia, atherosclerosis, and various diseases caused by such diseases can include hyperlipidemia, arteriosclerosis, cervical or cerebral arteriosclerosis, cerebrovascular disease, cerebral infarction, stroke, reperfusion injuries, ischemic heart diseases, myocardial infarction, coronary sclerosis, nephrosclerosis, arteriosclerotic nephrosclerosis, arteriolar nephrosclerosis, malignant nephrosclerosis, ischemic enteropathy, acute mesenteric vessel occlusion, chronic intestinal angina, ischemic colitis, aortic aneurysm, arteriosclerosis obliterans (ASO), and fatty liver.

The medicine according to the present invention contains the invention compound (1) or its salt as an active ingredient, and can be used either singly or in combination with one or more other medicinal ingredients or one or more medicinal ingredients having different action mechanisms. Further, the invention compound (1) or its salt can also be administered as a medicinal composition with a pharmacologically acceptable carrier added therein as needed, and hence, can be formulated into a medicinal composition (preparation). Namely, the medicinal composition according to the present invention is characterized in that it contains the compound represented by the formula (1) and/or its salt. Examples of the term "composition (preparation)" as used herein can include inhalations, injections, oral preparations, perrectal preparations, and transdermal preparations. Pharmacologically acceptable carriers which can be incorporated in these compositions are, for example, excipients, binders, coating materials, lubricants, sugarcoating materials, disintegrators, extenders, correctives, emulsifiers, solubilizers, dispersants, stabilizer, pH adjusters, and isotonicities.

The preferred dosage of the medicine according to the present invention differs depending on the condition, the kind of disease, the sex, the age, the physique and the like, but in terms of the invention compound (1) or its salt, it is generally preferred to administer 1 to 1,000 mg in one to several portions per adult and day.

EXAMPLES

The present invention will hereinafter be described in further detail on the basis of Examples, needless to say, the present invention shall by no means be limited only to the following Examples.

Example 1

N-(2,6-Diisopropylphenyl)-N'-pentyl-N'-[[2'-(1H-tetrazol-5-yl)-1,1'-biphenyl-4-yl]methyl]urea

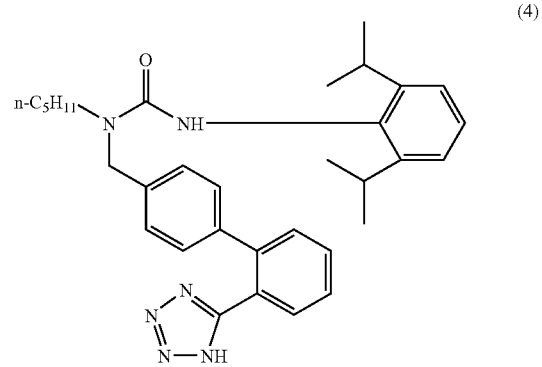

(4)

n-Pentylamine (129.6 mg) and triethylamine (170 mg) were dissolved in dimethylformamide (3 mL) and under ice bath cooling, [[2'-[N-(triphenylmethyl)tetrazol-5-yl]-1,1'-biphenyl-4-yl]methyl] bromide (399.8 mg) was added, and then the mixture was stirred at room temperature. Forty-eight hours later, ethyl acetate (30 mL) was added, and the resulting mixture was washed three times with brine (50 mL, each). The organic layer was dried over anhydrous sodium sulfate and concentrated under reduced pressure. The residue and phenyl 2,6-diisopropylphenylcarbamate (216.9 mg) were dissolved in toluene (10 mL), and the solution was heated under reflux. Two hours later, the reaction mixture was concentrated under reduced pressure. The residue was subjected to chromatography on a silica gel column (hexane/ethyl acetate) to afford N-(2,6-diisopropylphenyl)-N'-pentyl-N'-[[2'-[N-(triphenylmethyl)tetrazol-5-yl]-1,1'-biphenyl-4-yl]methyl]urea (88.6 mg). Yield: 16%.

$^1$H-NMR (CDCl$_3$, ppm):
0.83-0.98(m,6H), 1.23-1.42(m,13H), 1.62-1.70(m,2H), 2.90-3.03(m,2H), 3.33(t,2H,J=7.29 Hz), 4.49(s,2H), 5.56(s,1H), 6.90-6.94(m,6H), 7.10-7.17(m,6H), 7.22-7.37(m,11H), 7.42-7.54(m,2H), 7.96(dd,1H,J=7.02 Hz,J=2.43 Hz).

N-(2,6-Diisopropylphenyl)-N'-pentyl-N'-[[2'-[N-(triphenylmethyl)tetrazol-5-yl]-1,1'-biphenyl-4-yl]methyl]urea (330 mg) was dissolved in tetrahydrofuran (4 mL). After addition of 10% hydrochloric acid (1.2 mL), the resulting mixture was stirred at room temperature. Seventeen hours later, the reaction mixture was concentrated at low temperature under reduced pressure. Water (10 mL) was added to the concentrate, followed by extraction three times with chloroform (12 mL, each). The organic layer was washed with brine (15 mL), dried over anhydrous sodium sulfate, and then concentrated under reduced pressure. The residue was subjected to chromatography on a silica gel column (chloroform/methanol) to afford the compound represented by the formula (4) (0.21 g). Yield: 93%.

$^1$H-NMR (CDCl$^3$, ppm):
0.91(t,3H,J=6.75 Hz), 0.97-1.12(m,12H), 1.31-1.42(m, 4H), 1.60-1.78(m,2H), 2.91-3.01(m,2H), 3.27(t,2H, J=7.83 Hz), 4.45(s,2H), 5.71(s,1H), 6.96-7.20(m,7H), 7.39-7.60(m,3H), 7.81(dd,1H,J=7.29 Hz,J=1.62 Hz).

m.p. 129-132° C.

IR (cm$^{-1}$) (KBr):
1255, 1510, 1609, 2868, 2930, 2960.

Example 2

N'-Pentyl-N'-[[2'-(1H-tetrazol-5-yl)-1,1'-biphenyl-4-yl]methyl]-N-(2,4,6-trimethylphenyl)urea

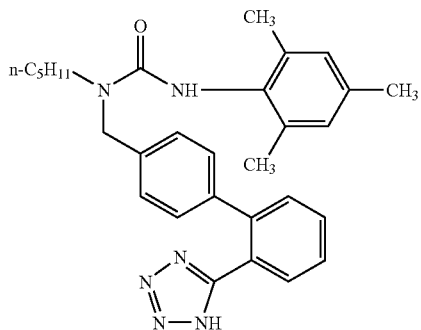

(5)

Using n-pentylamine (304.2 mg), triethylamine (442.2 mg), [[2'-(N-(triphenylmethyl)tetrazol-5-yl]-1,1'-biphenyl-4-yl]methyl] bromide (400 mg) and phenyl 2,4,6-trimethylphenylcarbamate (233.8 mg), N'-pentyl-N-(2,4,6-trimethylphenyl)-N'-[[2'-[N-(triphenylmethyl)tetrazol-5-yl]-1,1'-biphenyl-4-yl]methyl]urea (113 mg) was obtained by a similar procedure as in Example 1. Yield: 22%.

$^1$H-NMR (CDCl$_3$, ppm):
0.88(t,3H,J=6.48 Hz), 1.18-1.35(m,4H), 1.61-1.69(m,2H), 2.05(s,3H), 2.23(s,6H), 3.30(t,2H,J=7.29 Hz), 4.49(s, 2H), 5.54(s,1H), 6.83-6.99(m,8H), 7.12-7.16(m,3H), 7.25-7.38(m,11H), 7.44-7.92(m,2H), 7.94(dd,1H, J=8.91 Hz,J=2.16 Hz).

N'-Pentyl-N-(2,4,6-trimethylphenyl)-N'-[[2'-[N-(triphenylmethyl)tetrazol-5-yl]-1,1'-biphenyl-4-yl ]methyl]urea (113 mg) was treated with hydrochloric acid in a similar manner as in Example 1 to afford the compound represented by the formula (5) (61.8 mg).
Yield: 82%.

$^1$H-NMR (CDCl$_3$, ppm):
0.88(t,3H,J=6.75 Hz), 1.22-1.35(m,4H), 1.55-1.72(m,2H), 2.00(s,6H), 2.14(s,3H), 3.21(t,2H,J=7.29 Hz), 4.23(s, 2H), 5.66(s,1H), 6.55(s,2H), 7.07-7.29(m,5H), 7.44-7.62(m,2H), 7.84(dd,1H,J=7.29 Hz,J=1.35 Hz).
m.p. 106-109° C.
IR (cm$^{-1}$) (KBr):
1240, 1466, 1600, 2928.

Example 3

N'-Pentyl-N'-[[2'-(1H-tetrazol-5-yl)-1,1'-biphenyl-4-yl]methyl]-N-(2,4,6-trifluorophenyl)urea

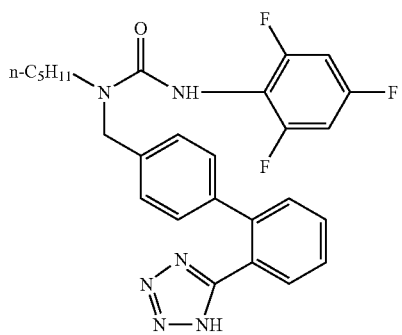

(6)

According to the procedure of Example 1, a secondary amine was produced from n-pentylamine (0.94 g) and [[2'-[N-(triphenylmethyl)tetrazol-5-yl]-1,1'-biphenyl-4-yl]methyl] bromide (1.50 g). Using the secondary amine and phenyl 2,4,6-trifluorophenylcarbamate (0.72 g), N'-pentyl-N-(2,4,6-triflurophenyl)-N'-[[2'-[N-(triphenylmethyl)tetrazol-5-yl]-1,1'-biphenyl-4-yl]methyl]urea was afforded (0.50 g). Yield: 25%.

$^1$H-NMR (CDCl$_3$, ppm):
0.89(t,3H,J=6.48 Hz), 1.23-1.36(m,4H), 1.50-1.66(m,2H), 3.21(t,2H,J=7.56 Hz), 4.49(s,2H), 5.54(s,1H), 6.65-6.73(m,2H), 6.90-7.53(m,22H), 7.94(dd,1H,J=7.02 Hz,J=1.89 Hz).

N'-Pentyl-N-(2,4,6-triflurophenyl)-N'-[[2'-[N-(triphenylmethyl)tetrazol-5-yl]-1,1'-biphenyl-4-yl]methyl]urea (173.2 mg) was treated with hydrochloric acid in a similar manner as in Example 1 to afford the compound represented by the formula (6) (60.2 mg). Yield: 52%.

$^1$H-NMR (CDCl$_3$, ppm):
0.89(t,3H,J=6.48 Hz), 1.26-1.31(m,4H), 1.55-1.65(m,2H), 3.28(t,2H,J=7.02 Hz), 4.41(s,2H), 6.14(s,1H), 6.51-6.57(m,2H), 6.90-7.65(m,7H), 7.82(d,1H,J=7.29 Hz).
m.p. 103-107° C.
IR (cm$^{-1}$) (KBr):
1449, 1521, 1612, 1629, 2931, 2958.

Example 4

N'-Heptyl-N'-[[2'-(1H-tetrazol-5-yl)-1,1'-biphenyl-4-yl]methyl]-N-(2,4,6-trifluorophenyl)urea

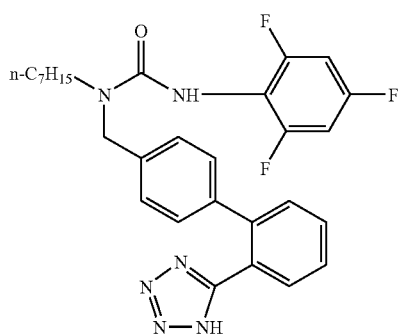

(7)

2,4,6-Trifluorobenzoic acid (148.8 mg), diphenylphosphoryl azide (223.3 mg) and triethylamine (105.1 mg) were added to benzene (8 mL) and the mixture was heated under reflux. Fifty minutes later, a solution of N-heptyl-N-[[2'-[N-(triphenylmethyl)tetrazol-5-yl]-1,1'-biphenyl-4-yl]methyl] amine (393.7 mg) in benzene (3 mL) was added to the reaction mixture, and under reflux, heating was continued. Upon elapsed time of 45 minutes after the addition of the solution, the reaction mixture was concentrated under reduced pressure. Ethyl acetate (40 mL) was added to the residue, and the resulting mixture was washed successively with 5% hydrochloric acid, water, a saturated sodium bicarbonate solution and brine (40 mL, each). The organic layer was dried over anhydrous sodium sulfate, and then concentrated under reduced pressure. The residue was subjected to chromatography on a silica gel column (hexane/ethyl acetate) to afford N'-heptyl-N-(2,4,6-trifluorophenyl)-N'-[[2'-[N-(triphenylmethyl)tetrazol-5-yl]-1,1'-biphenyl-4-yl]methyl]urea as a colorless amorphous mass (369.1 mg).

Yield: 74%.

¹H-NMR (CDCl₃, ppm):
0.87(t,3H,J=6.21 Hz), 1.15-1.35(m,8H), 1.50-1.60(m,2H), 3.20(t,2H,J=7.29 Hz), 4.48(s,2H), 5.62(s,1H), 6.62-6.76(m,2H), 6.89-6.98(m,6H), 7.06-7.16(m,4H), 7.22-7.53(m,12H), 7.93(dd,1H,J=7.02 Hz,J=1.62 Hz).

N'-Heptyl-N-(2,4,6-trifluorophenyl)-N'-[[2'-[N-(triphenylmethyl)tetrazol-5-yl]-1,1'-biphenyl-4-yl]methyl]urea (437.5 mg) was treated with hydrochloric acid in a similar manner as in Example 1 to afford the compound represented by the formula (7) (219.1 mg).

Yield: 73%.

¹H-NMR (CDCl₃, ppm):
0.88(t,3H,J=6.48 Hz), 1.15-1.47(m,8H), 1.55-1.75(m,2H), 3.10(t,2H,J=7.56 Hz), 4.54(s,2H), 5.89(s,1H), 6.58(dd, 2H,J=7.29 Hz,J=8.37 Hz), 7.11-7.26(m,4H), 7.40-7.61 (m,3H), 7.93(dd,1H,J=7.29 Hz,J=1.62 Hz).

m.p. 86-89° C.

IR (cm⁻¹) (KBr):
1521, 1615, 1625, 2929.

Example 5

N-(2,4-Difluorophenyl)-N'-heptyl-N'-[[2'-(1H-tetrazol-5-yl)-1,1'-biphenyl-4-yl]methyl]urea

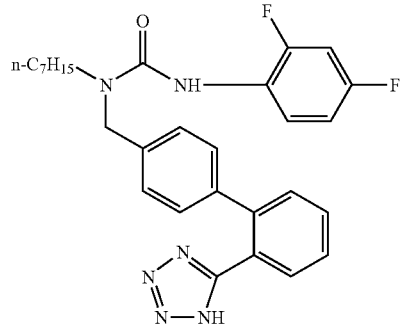

(8)

n-Heptylamine (3.96 g) and potassium carbonate (0.91 g) were added to dimethylformamide (60 mL), and under ice cooling, [[2'-[N-(triphenylmethyl)tetrazol-5-yl]-1,1'-biphenyl-4-yl]methyl] bromide (4.00 g) was added. The resulting mixture was stirred at the same temperature for a while, and was then stirred at room temperature. Forty-five hours later, ethyl acetate (150 mL) was added. The mixture was washed once with water (500 mL) and four times with brine (500 mL, each), dried over anhydrous sodium sulfate, and then concentrated under reduced pressure. Toluene (100 mL) and 2,4-difluorophenyl isocyanate (1.33 g) were added to the residue and the mixture was heated under reflux. Eighty minutes later, the mixture was diluted with toluene (100 mL), and then washed successively with a saturated sodium bicarbonate solution (100 mL) and brine (100 mL). The organic layer was dried over anhydrous sodium sulfate and then concentrated under reduced pressure. The residue was subjected to chromatography on a silica gel column (hexane/ethyl acetate) to afford N-(2,4-difluorophenyl)-N'-heptyl-N'-[[2'-[N-(triphenylmethyl)tetrazol-5-yl]-1,1'-biphenyl-4-yl]methyl]urea as a pale yellow oil (3.15 g). Yield: 59%.

¹H-NMR (CDCl₃, ppm): 0.88(t,3H,J=6.48 Hz), 1.15-1.35 (m,8H), 1.57-1.60(m,2H), 3.19(t,2H,J=7.29 Hz), 4.46(s,2H), 6.37(d,1H,J=3.24 Hz), 6.73-6.93(m,11H), 7.04-7.53(m, 13H), 7.94(dd,1H,J=7.56 Hz,J=1.62 Hz), 8.02-8.11(m,1H).

N-(2,4-Difluorophenyl)-N'-heptyl-N'-[[2'-[N-(triphenylmethyl)tetrazol-5-yl]-1,1'-biphenyl-4-yl]methyl]urea (1.05 g) was treated with hydrochloric acid in a similar manner as in Example 1 to afford the compound represented by the formula (8) (0.34 g). Yield: 59%.

¹H-NMR (CDCl₃, ppm):
0.88(t,3H,J=6.48 Hz), 1.22-1.33(m,8H), 1.58-1.75(m,2H), 3.30(t,2H,J=7.83 Hz), 4.53(s,2H), 6.45(d,1H,J=3.51 Hz), 6.70-6.87(m,2H), 7.14-7.32(m,4H), 7.34-7.65(m, 3H), 7.76-7.85(m,1H), 7.98(d,1H,J=7.56 Hz)

IR (cm⁻¹) (KBr):
1516, 1624, 1612.

Example 6

N-Cyclohexyl-N'-heptyl-N'-[[2'-(1H-tetrazol-5-yl)-1,1'-biphenyl-4-yl]methyl]urea

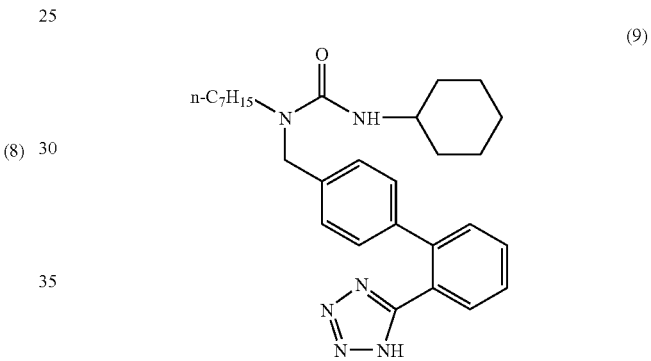

(9)

Using n-heptylamine (192 mg), [[2'-[N-(triphenylmethyl)tetrazol-5-yl]-1,1'-biphenyl-4-yl]methyl] bromide (843 mg) and cyclohexyl isocyanate (230 mg), N-cyclohexyl-N'-heptyl-N'-[[2'-[N-(triphenylmethyl)tetrazol-5-yl]-1,1'-biphenyl-4-yl]methyl]urea (0.53 g) was obtained in a similar manner as in Example 5. Yield: 49%.

¹H-NMR (CDCl₃, ppm):
0.87(t,3H,J=6.75 Hz), 0.94-1.40(m,12H), 1.48-1.62(m, 6H), 1.85-1.90(m,2H), 3.06(t,2H,J=7.83 Hz), 3.61-3.71 (m,1H), 4.13(d,1H), 4.34(s,2H), 6.86-6.94(m,6H), 7.00-7.12(m,4H), 7.17-7.53(m,12H), 7.91(dd,1H, J=6.75 Hz,J=1.35 Hz).

N-Cyclohexyl-N'-heptyl-N'-[[2'-[N-(triphenylmethyl)tetrazol-5-yl]-1,1'-biphenyl-4-yl]methyl]urea (0.53 g) was treated with hydrochloric acid in a similar manner as in Example 1 to afford the compound represented by the formula (9) (0.24 g). Yield: 69%.

¹H-NMR (CDCl₃, ppm):
0.87(t,3H,J=6.75 Hz), 0.93-1.38(m,15H), 1.51-1.66(m, 3H), 1.72-1.80(m,2H), 3.06(t,2H,J=7.83 Hz), 3.35-3.52 (m,1H), 4.14(d,1H,J=7.29 Hz), 4.37(s,2H), 7.12(s,4H), 7.42-7.65(m,3H), 7.90(dd,1H,J=6.75 Hz,J=1.35 Hz).

IR (cm⁻¹) (KBr):
1532, 2930.

Example 7

N'-Pentyl-N'-[[2'-[[(trifluoromethyl)carbonyl]-amino]-1,1'-biphenyl-4-yl]methyl]-N-(2,4,6-trifluorophenyl)urea

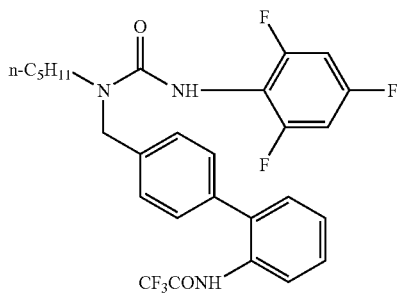

(10)

n-Amylamine (0.54 g) and potassium carbonate (0.98 g) were suspended in dimethylformamide (3.5 mL), and [[2'-nitro-1,1'-biphenyl-4-yl]methyl] bromide (0.51 g) was added in portions. Four hours later, ethyl acetate (20 mL) was added, and the resulting mixture was washed once with water (40 mL) and twice with brine (90 mL, each). The organic layer was dried over anhydrous sodium sulfate and then concentrated under reduced pressure. The residue was subjected to chromatography on a silica gel column (chloroform/ethyl acetate) to afford N-[(2'-nitro-1,1'-biphenyl-4-yl)methyl]-N-pentylamine as a yellow oil (0.40 g). Yield: 77%.

Using 2,4,6-trifluorobenzoic acid (0.43 g), diphenylphosphoryl azide (0.68 g), triethylamine (0.25 g) and N-[(2'-nitro-1,1'-biphenyl-4-yl)methyl]-N-pentylamine (0.40 g), N'-[(2'-nitro-1,1'-biphenyl-4-yl)methyl]-N'-pentyl-N-(2,4,6-trifluorophenyl)urea (0.60 g) was obtained by a similar procedure as in Example 4. Yield: 95%.

$^1$H-NMR (CDCl$_3$, ppm):
0.94(t,3H,J=7.02 Hz), 1.20-1.49(m,4H), 1.59-1.75(m,2H), 3.42(t,2H,J=7.83 Hz), 4.64(s,2H), 5.74(s,1H), 6.64-6.87(m,4H), 7.09-7.65(m,6H).

N'-[(2'-Nitro-1,1'-biphenyl-4-yl)methyl]-N'-pentyl-N-(2,4,6-trifluorophenyl)urea (196.0 mg) and anhydrous tin(II) chloride (401.6 mg) were added to ethanol (4 mL), and the mixture was heated under reflux. One hour later, the solvent was distilled off, and ethyl acetate (15 mL) and a saturated sodium bicarbonate solution (15 mL) were added to the residue. The resultant precipitate was filtered off through Celite. The filtrate was extracted with ethyl acetate. The organic layer was dried over anhydrous sodium sulfate and concentrated under reduced pressure to afford N'-[(2'-amino-1,1'-biphenyl-4-yl)methyl]-N'-pentyl-N-(2,4,6-trifluorophenyl)urea (179.2 mg). Yield: 94%.

N'-[(2'-Amino-1,1'-biphenyl-4-yl)methyl]-N'-pentyl-N-(2,4,6-trifluorophenyl)urea (179.2 mg) was dissolved in pyridine (1.5 mL), and after addition of trifluoroacetic anhydride (0.15 mL), the mixture was stirred at room temperature. Thirty minutes later, ethyl acetate (15 mL) was added, and the resulting mixture was washed successively with water (15 mL), brine (30 mL), a saturated sodium bicarbonate solution (30 mL) and brine (30 mL). The organic layer was dried over anhydrous sodium sulfate and then concentrated under reduced pressure. The residue was subjected to chromatography on a silica gel column (hexane/ethyl acetate) to afford the compound represented by the formula (10) as a colorless amorphous mass (129.5 mg). Yield: 58%.

$^1$H-NMR (CDCl$_3$, ppm):
0.94(t,3H,J=7.02 Hz), 1.32-1.78(m,4H), 1.62-1.72(m,2H), 3.41(t,2H,J=7.29 Hz), 4.68(s,2H), 5.73(s,1H), 6.66-6.77(m,2H), 7.20-7.49(m,7H), 7.95(bs,1H), 8.23(d,1H, J=8.10 Hz).

IR (cm$^{-1}$) (KBr): 1202, 1521, 1636.

Example 8

N'-Pentyl-N'-[[2'-[[(trifluoromethyl)sulfonyl]-amino]-1,1'-biphenyl-4-yl]methyl]-N-(2,4,6-trifluorophenyl)urea

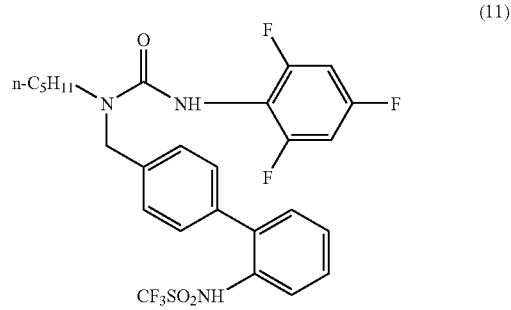

(11)

N'-[(2'-Amino-1,1'-biphenyl-4-yl)methyl]-N'-pentyl-N-(2,4,6-trifluorophenyl)urea (100 mg) was dissolved in dichloromethane (2 mL), and while maintaining the solution at −10 to −5° C., a solution of trifluoromethanesulfonic acid anhydride (70 mg) in dichloromethane (2 mL) was added dropwise. After the resulting mixture was stirred at the same temperature for 4 hours, chloroform (20 mL) was added and the mixture was washed with a saturated sodium bicarbonate solution (20 mL). The aqueous layer was extracted further with chloroform (10 mL). The combined organic layers were dried over anhydrous sodium sulfate and then concentrated under reduced pressure. The residue was purified by chromatography on a silica gel column (chloroform/methanol) to afford the compound represented by the formula (11) (60 mg). Yield: 46%.

$^1$H-NMR (CDCl$_3$, ppm):
0.92(t,3H,J=6.75 Hz), 1.32-1.38(m,4H), 1.68-1.78(m,2H), 3.41(t,2H,J=7.56 Hz), 4.68(s,2H), 5.73(s,1H), 6.66-6.77(m,2H), 7.31-7.49(m,7H), 7.95(s,1H), 8.28(d,1H, J=7.83 Hz).

IR (cm$^{-1}$):
1202, 1521, 1636.

Example 9

N'-[[2'-[[[[(2,6-Diisopropylphenyl)amino]-carbonyl]amino]sulfonyl]-1,1'-biphenyl-4-yl]methyl]-N'-heptyl-N-(2,4,6-trifluorophenyl)urea

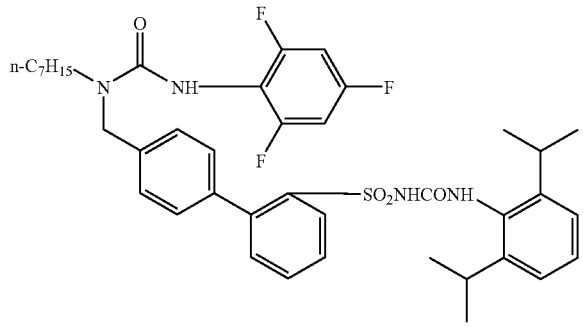

(12)

[[2'-[(t-Butylamino)sulfonyl]-1,1'-biphenyl-4-yl]methyl] bromide (0.94 g), n-heptylamine (0.28 g) and potassium carbonate (0.35 g) were added to dimethylformamide and the mixture was stirred at room temperature. Sixteen hours and 30 minutes later, ethyl acetate (30 mL) was added, and the resulting mixture was washed three times with brine (100 mL, each). The organic layer was dried over anhydrous sodium sulfate and then concentrated under reduced pressure. The residue was subjected to chromatography on a silica gel column (chloroform/ethyl acetate) to afford N-[[2'-[(t-butylamino)sulfonyl]-1,1'-biphenyl-4-yl]methyl]-N-heptylamine as a yellow oil (0.43 g). Yield: 42%.

$^1$H-NMR (CDCl$_3$, ppm):
0.89(t,3H,J=7.02 Hz), 0.99(s,9H), 1.22-1.31(m,6H), 1.45-1.60(m,4H), 2.64(t,2H,J=6.75 Hz), 3.56(s,1H), 4.86(s,2H), 7.30-7.65(m,7H), 8.17(dd,1H,J=7.83 Hz,J=1.35 Hz).

Using 2,4,6-trifluorobenzoic acid (0.27 g), diphenylphosphoryl azide (0.44 g), triethylamine (0.17 g) and N-[[2'-[(t-butylamino)sulfonyl]-1,1'-biphenyl-4-yl]methyl]-N-heptylamine (0.43 g), N'-[[2'-[(t-butylamino)sulfonyl]-1,1'-biphenyl-4-yl]methyl]-N'-heptyl-N-(2,4,6-trifluorophenyl)urea was afforded as colorless crystals (0.49 g) by a similar procedure as in Example 4. Yield: 81%.

$^1$H-NMR (CDCl$_3$, ppm):
0.89(t,3H,J=7.02 Hz), 0.95(s,9H), 1.22-1.35(m,4H), 1.52-1.58(m,2H), 1.66-1.78(m,2H), 3.39(t,2H,J=8.10 Hz), 3.56(s,1H), 4.66(s,2H), 5.74(s,1H), 6.66-6.77(m,2H), 7.20-7.65(m,7H), 8.17(dd,1H,J=7.29 Hz,J=1.08 Hz).

N'-[[2'-[(t-Butylamino)sulfonyl]-1,1'-biphenyl-4-yl]methyl]-N'-heptyl-N-(2,4,6-trifluorophenyl)urea (0.49 g) was dissolved in trifluoroacetic acid (8 mL), and after addition of anisole (0.36 mL), the resulting mixture was stirred at room temperature. Twenty-four hours later, ethyl acetate (40 mL) was added to the reaction mixture, and the mixture was washed with a saturated sodium bicarbonate solution (60 mL) and brine (60 mL). The organic layer was dried over anhydrous sodium sulfate and then concentrated under reduced pressure. The residue was subjected to chromatography on a silica gel column (hexane/ethyl acetate) to afford N'-[[(2'-aminosulfonyl)-1,1'-biphenyl-4-yl]methyl]-N'-heptyl-N-(2,4,6-trifluorophenyl)urea (0.40 g) as a colorless amorphous mass. Yield: 90%.

$^1$H-NMR (CDCl$_3$, ppm):
0.89(t,3H,J=6.48 Hz), 1.23-1.35(m,8H), 1.65-1.73(m,2H), 3.41(t,2H,J=7.29 Hz), 4.25(s,2H), 4.66(s,2H), 5.81(s,1H), 6.66-6.72(m,2H), 7.31-7.63(m,7H), 8.14(dd,1H, J=7.83 Hz,J=1.08 Hz).

N'-[[(2'-Aminosulfonyl)-1,1'-biphenyl-4-yl]methyl]-N'-heptyl-N-(2,4,6-trifluorophenyl)urea (0.40 g) and 2,6-diisopropylphenyl isocyanate (0.22 g) were added to acetone (15 mL) and the mixture was heated under reflux. Fifty minutes later, the reaction mixture was concentrated under reduced pressure and an aqueous solution of potassium dihydrogenphosphate was added to the residue to adjust the pH to 4 to 5. The resulting mixture was extracted with ethyl acetate (40 mL), and the organic layer was dried over anhydrous sodium sulfate and then concentrated under reduced pressure. The residue was subjected to chromatography on a silica gel column (hexane/ethyl acetate) to afford the compound represented by the formula (12) in the form of a colorless amorphous mass (0.41 g). Yield: 74%.

$^1$H-NMR (CDCl$_3$, ppm):
0.88(t,3H,J=6.75 Hz), 0.99(d,12H,J=6.75 Hz), 1.23-1.34(m,8H), 1.62-1.78(m,2H), 2.51(m,2H), 3.43(t,2H,J=7.56 Hz), 4.67(s,2H), 5.76(s,1H), 6.63-6.74(m,2H), 7.07(d,2H,J=8.10 Hz), 7.16-7.66(m,8H), 8.25(d,1H, J=7.02 Hz).
m.p. 89-93° C.
IR (cm$^{-1}$) (KBr):
1121, 1502, 1521, 1636.

Example 10

N-[[[(2,6-Diisopropylphenyl)amino]carbonyl]methyl]-N-pentyl-N-[[2'-(1H-tetrazol-5-yl)-1,1'-biphenyl-4-yl]methyl]amine

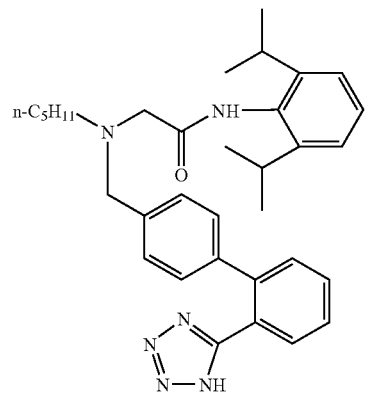

(13)

[[2'-[N-(Triphenylmethyl)tetrazol-5-yl)-1,1'-biphenyl-4-yl]methyl] bromide (2.32 g) and sodium azide (0.59 g) were suspended in a mixed solution of dimethylformamide (8 mL) and water (0.4 mL), and then the mixture was stirred at room temperature. Twenty-two hours later, ethyl acetate (100 mL) was added, and the resulting mixture was washed three times with brine (300 mL, each). The organic layer was dried over anhydrous sodium sulfate and concentrated under reduced pressure. The residue was dissolved in tetrahydrofuran (40 mL), and under ice bath cooling, lithium aluminum hydride (322.0 mg) was added. The mixture was stirred at room temperature for 1 hour, and under ice bath cooling, water (8 mL), a 10% aqueous solution of sodium hydroxide (8 mL)

and water (8 mL) were added successively. The resulting precipitate was filtered off, and the filtrate was concentrated under reduced pressure. Water (80 mL) was added to the residue, and the mixture was extracted twice with chloroform (60 mL, each). The organic layers were combined and then washed with brine (100 mL). The organic layer was dried over anhydrous sodium sulfate and concentrated under reduced pressure. The residue was dissolved in dichloromethane (30 mL), and after addition of triethylamine (1500 mg) and valeroyl chloride (1.80 g), the mixture was stirred under ice bath cooling. Forty minutes later, chloroform (50 mL) was added to the reaction mixture, and the resulting mixture was washed with a saturated sodium bicarbonate solution (100 mL) and brine (100 mL). The organic layer was dried over anhydrous sodium sulfate and concentrated under reduced pressure. The residue was subjected to chromatography on a silica gel column (hexane/ethyl acetate) to afford N-pentanoyl-N-[[2'-[N-(triphenylmethyl)tetrazol-5-yl]-1,1'-biphenyl-4-yl]methyl] amine as colorless crystals (1.61 g). Yield: 67%.

$^1$H-NMR (CDCl$_3$, ppm):
0.90(t,3H,J=7.29 Hz), 1.23-1.37(m,2H), 1.55-1.66(m,2H), 2.10(t,2H,J=8.10 Hz), 4.32(d,2H,J=5.40 Hz), 5.41(bs, 1H), 6.88-7.53(m,22H), 7.96(dd,1H,J=6.75 Hz,J=2.16 Hz).

N-Pentanoyl-N-[[2'-[N-(triphenylmethyl)tetrazol-5-yl]-1, 1'-biphenyl-4-yl]methyl]amine (1.61 g) was dissolved in tetrahydrofuran (40 mL) and at room temperature, lithium aluminum hydride (340.1 mg) was added, and then the mixture was heated under reflux. Ninety minutes later, water (5 mL), a 10% aqueous solution of sodium hydroxide (5 mL) and water (5 mL) were added successively under ice bath cooling. The organic layer was separated, dried over anhydrous sodium sulfate, and then concentrated under reduced pressure. As water remained to the residue, ethyl acetate was added to conduct extraction twice from the remaining water. The organic layer was dried over anhydrous sodium sulfate, and then concentrated under reduced pressure to afford N-pentyl-N-[[2'-[N-(triphenylmethyl)tetrazol-5-yl]-1,1'-biphenyl-4-yl]methyl] amine (1.57 g). Yield: 100%.

N-(Chloroacetyl)-2,6-diisopropylaniline (196.3 mg), N-pentyl-N-[[2'-[N-(triphenylmethyl)tetrazol-5-yl]-1,1'-biphenyl-4-yl]methyl]amine (430.0 mg), potassium iodide (70 mg) and triethylamine (0.6 g) were suspended in dimethylformamide (3 mL). The resulting mixture was heated to about 80° C., and then stirred at that temperature. Three hours later, the reaction mixture was cooled, ethyl acetate (30 mL) was added, and the mixture was washed four times with brine (50 mL, each). The organic layer was dried over anhydrous sodium sulfate and concentrated under reduced pressure. The residue was subjected to chromatography on a silica gel column (hexane/ethyl acetate) to afford N-[[[(2,6-diisopropylphenyl)amino]carbonyl]methyl]-N-pentyl-N-[[2'-[N-(triphenylmethyl)tetrazol-5-yl]-1,1'-biphenyl-4-yl]methyl]amine (196.4 mg). Yield: 33%.

$^1$H-NMR (CDCl$_3$, ppm):
0.90(t,3H,J=7.02 Hz), 1.13(d,12H,J=7.02 Hz), 1.24-1.41 (m,4H), 1.55-1.65(m,2H), 2.60(t,2H,J=7.83 Hz), 2.63-2.98(m,2H), 3.24(s,2H), 3.62(s,2H), 6.90-6.94(m,6H), 7.07-7.55(m,19H), 7.93(dd,1H,J=6.48 Hz,J=1.08 Hz), 8.63(s,1H).

N-[[[(2,6-Diisopropylphenyl)amino]carbonyl]methyl]-N-pentyl-N-[[2'-[N-(triphenylmethyl)tetrazol-5-yl]-1,1'-biphenyl-4-yl]methyl]amine (278.3 mg) was dissolved in tetrahydrofuran (10 mL), and after addition of 10% hydrochloric acid (3.0 mL), the resulting mixture was stirred at room temperature. Nineteen hours later, the solvent was distilled off, and to the residue, water (30 mL) was added. The mixture so obtained was extracted twice with chloroform (30 mL, each). The organic layer was dried over anhydrous sodium sulfate and concentrated under reduced pressure. The residue was subjected to chromatography on a silica gel column (chloroform/methanol) to afford N-[[[(2,6-diisopropylphenyl) amino]carbonyl]methyl]-N-pentyl-N-[[2'-(1H-tetrazol-5-yl)-1,1'-biphenyl-4-yl]methyl]amine hydrochloride as pale yellow crystals (190.6 mg). Yield: 93%.

$^1$H-NMR (CDCl$_3$, ppm):
0.90(t,3H,J=6.48 Hz), 1.12(d,12H,J=7.02 Hz), 1.25-1.43 (m,4H), 1.85(bs,2H), 2.89-2.99(m,2H), 3.20(bs,2H), 3.83(bs,2H), 4.32(bs,2H), 7.10-7.16(m,4H), 7.25-7.31 (m,1H), 7.39-7.59(m,5H), 7.91(dd,1H,J=7.29 Hz,J=1.35 Hz), 9.23(bs,1H).

m.p. 102-107° C.
IR (cm$^{-1}$) (KBr):
1459, 1471, 1687, 2869, 2930, 2962.

N-[[[(2,6-Diisopropylphenyl)amino]carbonyl]methyl]-N-pentyl-N-[[2'-(1H-tetrazol-5-yl)-1,1'-biphenyl-4-yl]methyl] amine hydrochloride (140.4 mg) was suspended in a saturated sodium bicarbonate solution (5 mL) and the mixture was stirred for 1 hour. The mixture was adjusted to pH 3 with dilute hydrochloric acid, and then extracted with ethyl acetate (30 mL). The organic layer was washed with brine. The organic layer was dried over anhydrous sodium sulfate and concentrated under reduced pressure to afford the compound represented by the formula (13) as a colorless solid (107.3 mg). Yield: 82%.

$^1$H-NMR (CDCl$_3$, ppm):
0.90(t,3H,J=6.75 Hz), 1.11(d,12H,J=7.02 Hz), 1.23-1.34 (m,4H), 2.74(t,2H,J=7.29 Hz), 2.86-2.96(m,2H), 3.33 (s,2H), 3.85(s,2H), 7.07-7.16(m,4H), 7.25-7.31(m,3H), 7.38-7.41(m,1H), 7.47-7.60(m,2H), 7.99(dd,1H,J=7.29 Hz,J=1.35 Hz), 8.77(s,1H).

m.p. 74-80° C.
IR (cm$^{-1}$) (KBr):
1459, 1505, 1658, 2869, 2930.

Example 11

N-Pentyl-N-[[2'-(1H-tetrazol-5-yl)-1,1'-biphenyl-4-yl]methyl]-N-[[[(2,4,6-trimethylphenyl)amino]-carbonyl]methyl]amine

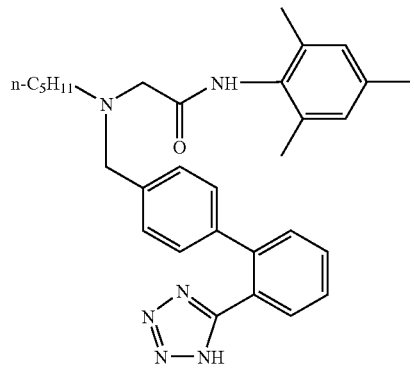

(14)

N-(Chloroacetyl)-2,4,6-trimethylaniline (443.2 mg), N-pentyl-N-[[2'-[N-(triphenylmethyl)tetrazol-5-yl]-1,1'-biphenyl-4-yl]methyl]amine (780.0 mg), potassium iodide (129.1 mg) and triethylamine (1.15 g) were suspended in dimethylformamide (6 mL). The resulting mixture was heated to about 80° C., and then stirred at that temperature. Three hours later, the reaction mixture was cooled, ethyl acetate (50 mL) was added, and the mixture was washed four times with brine (100 mL, each). The organic layer was dried over anhydrous sodium sulfate and concentrated under reduced pressure. The residue was subjected to chromatography on a silica gel column (hexane/ethyl acetate) to afford N-pentyl-N-[[[(2,4,6-trimethylphenyl)amino]carbonyl]methyl]-N-[[2'-[N-(triphenylmethyl)tetrazol-5-yl]-1,1'-biphenyl-4-yl]methyl]amine (395.4 mg). Yield: 39%.

$^1$H-NMR (CDCl$_3$, ppm):
0.89(t,3H,J=7.02 Hz), 1.23-1.31(m,4H), 1.45-1.65(m,2H), 2.08(s,6H), 2.26(s,3H), 2.59(t,2H,J=7.83 Hz), 3.24(s,2H), 3.62(s,2H), 6.89-7.54(m,24H), 7.92(dd,1H,J=7.02 Hz,J=1.89 Hz), 8.59(s,1H).

N-Pentyl-N-[[[(2,4,6-timethylphenyl)amino]-carbonyl]methyl]-N-[[2'-[N-(triphenylmethyl)tetrazol-5-yl]-1,1'-biphenyl-4-yl]methyl]amine (395.4 mg) was dissolved in tetrahydrofuran (25 mL), and after addition of 10% hydrochloric acid, the resulting mixture was stirred for 18 hours and 30 minutes. The solvent was then distilled off under reduced pressure. To the residue, water (45 mL) was added, and the mixture was extracted twice with ethyl acetate (45 mL, each). The organic layer was dried over anhydrous sodium sulfate and concentrated under reduced pressure. The residue was subjected to chromatography on a silica gel column (chloroform/methanol). Relevant fractions (the hydrochloride) were concentrated, and after addition of a small amount of methanol to the residue, the mixture was stirred together with a saturated sodium bicarbonate solution (6 mL) for 1 hour. Under ice bath cooling, the solution was adjusted to pH 3 with dilute hydrochloric acid. Ethyl acetate (30 mL) was added, and the resulting mixture was washed six times with brine (50 mL, each). The organic layer was dried over anhydrous sodium sulfate and concentrated under reduced pressure. The residue was subjected to chromatography on a silica gel column (chloroform/methanol) to afford the compound represented by the formula (14) as colorless crystals (188.4 mg).

Yield: 69%.
$^1$H-NMR (CDCl$_3$, ppm):
0.89(t,3H,J=6.75 Hz), 1.23-1.43(m,4H), 1.56-1.72(m,2H), 2.02(s,6H), 2.22(s,3H), 2.69(t,2H,J=7.29 Hz), 3.24(s,2H), 3.78(s,2H), 6.81(s,2H), 7.04(d,2H,J=7.83 Hz), 7.22-7.57(m,5H), 7.95(d,1H,J=7.29 Hz), 8.68(s,1H).
m.p. 73-77° C.
IR (cm$^{-1}$) (KBr):
1505, 1659, 2928, 2956.

Example 12

N-Pentyl-N-[[2'-(1H-tetrazol-5-yl)-1,1'-biphenyl-4-yl]methyl]-N-[[[(2,4,6-trifluorophenyl)amino]-carbonyl]methyl]amine (15)

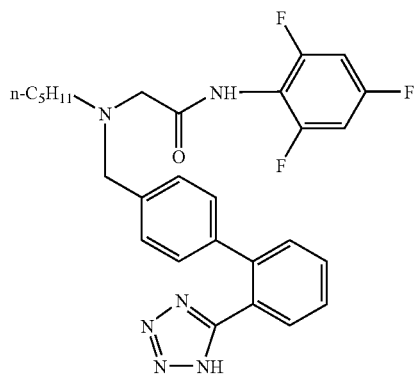

N-(Chloroacetyl)-2,4,6-trifluoroaniline (313.0 mg), N-pentyl-N-[[2'-[N-(triphenylmethyl)tetrazol-5-yl]-1,1'-biphenyl-4-yl]methyl]amine (780.0 mg), potassium iodide (230 mg) and triethylamine (2.1 g) were suspended in dimethylformamide (12 mL). The resulting mixture was heated to about 80° C., and then stirred at that temperature. Three hours later, the reaction mixture was cooled, ethyl acetate (100 mL) was added, and the mixture was washed four times with brine (200 mL, each). The organic layer was dried over anhydrous sodium sulfate and concentrated under reduced pressure. The residue was subjected to chromatography on a silica gel column (hexane/ethyl acetate) to afford N-pentyl-N-[[[(2,4,6-trifluorophenyl)amino]carbonyl]methyl]-N-[[2'-[N-(triphenylmethyl)tetrazol-5-yl]-1,1'-biphenyl-4-yl]methyl]amine (434.8 mg). Yield: 42%.

$^1$H-NMR (CDCl$_3$, ppm):
0.88(t,3H,J=7.02 Hz), 1.18-1.38(m,4H), 1.48-1.60(m,2H), 2.54(t,2H,J=7.56 Hz), 3.23(s,2H), 3.61(s,2H), 6.71-6.77(m,2H), 6.89-6.92(m,6H), 7.05-7.13(m,4H), 7.21-7.51(m,11H), 7.92(d,1H,J=5.94 Hz), 7.93(d,1H,J=5.94 Hz), 8.63(s,1H).

N-Pentyl-N-[[[(2,4,6-trifluorophenyl)amino]-carbonyl]methyl]-N-[[2'-[N-(triphenylmethyl)tetrazol-5-yl]-1,1'-biphenyl-4-yl]methyl]amine (425.8 mg) was dissolved in tetrahydrofuran (25 mL), and after addition of 10% hydrochloric acid, the resulting mixture was stirred for 18 hours and 30 minutes. The solvent was then distilled off under reduced pressure. To the residue, water (45 mL) was added, and the mixture was extracted twice with ethyl acetate (45 mL, each). The organic layer was dried over anhydrous sodium sulfate and concentrated under reduced pressure. The residue was subjected to chromatography on a silica gel column (chloroform/methanol). Relevant fractions (the hydrochloride) were concentrated, and after addition of a small amount of methanol to the residue, the mixture was stirred together with a saturated sodium bicarbonate solution (6 mL) for 1 hour. Under ice bath cooling, the solution was then adjusted to pH 3 with dilute hydrochloric acid. Ethyl acetate (30 mL) was added, and the resulting mixture was washed six times with brine (50 mL, each). The organic layer was dried over anhydrous sodium sulfate and concentrated under reduced pressure. The residue was subjected to chromatography on a silica gel column (chloroform/methanol) to afford the compound represented by the formula (15) (185.3 mg). Yield: 63%.

$^1$H-NMR (CDCl$_3$, ppm):
0.88(t,3H,J=6.48 Hz), 1.15-1.50(m,4H), 1.51-1.75(m,2H), 2.73(t,2H,J=7.83 Hz), 3.31(s,2H), 3.80(s,2H), 6.65-6.74(m,2H), 7.04(d,2H,J=7.83 Hz), 7.21-7.27(m,2H), 7.38-7.57(m,3H), 7.90(dd,1H,J=7.83 Hz,J=1.08 Hz), 8.93(s,1H).

m.p. 69-73° C.

IR (cm$^{-1}$) (KBr):
1449, 1521, 1610, 2932, 2957.

Example 13

N-[[[[(2,6-Diisopropylphenyl)amino]carbonyl]-amino]sulfonyl]-N-pentyl-N-[2'-[(1H-tetrazol-5-yl)-1,1'-biphenyl-4-yl]methyl]amine

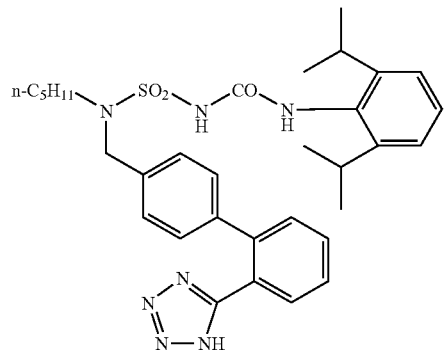

(16)

Chlorosulfonyl isocyanate (2.43 g) was dissolved in diethyl ether (10 mL), and at −15° C., the solution was added dropwise to a solution of 2,6-diisopropylaniline in diethyl ether (15 mL). After the mixture was stirred at the same temperature for 1 hour and 30 minutes, the resulting precipitates were collected by filtration and then washed with hexane. Colorless crystals so obtained were dried to afford [[[(2,6-diisopropylphenyl)amino]-carbonyl]amino]sulfonyl chloride (4.11 g). Yield: 75%.

$^1$H-NMR (CDCl$_3$, ppm):
1.22(s,6H), 1.25(s,6H), 3.13(m,2H), 7.20-7.39(m,3H), 7.76(s,1H)
m.p. 131-133° C.

[[2'-[N-(Triphenylmethyl)tetrazol-5-yl]-1,1'-biphenyl-4-yl]methyl] bromide (1.08 g), n-pentylamine (0.18 g) and potassium carbonate (0.45 g) were added to N,N-dimethylformamide (7 mL) and the mixture was stirred at room temperature. Sixteen hours later, ethyl acetate (40 mL) was added. The organic layer was washed with brine (140 mL×3 times). The organic layer was dried over anhydrous sodium sulfate and then concentrated under reduced pressure. To the residue, triethylamine (0.20 g) and tetrahydrofuran (11 mL) were added. Into the mixture, a solution of [[[(2,6-diisopropylphenyl)amino]carbonyl]amino]sulfonyl chloride (4.11 g) in tetrahydrofuran (9 mL) was added dropwise at room temperature. Two hours later, ethyl acetate (80 mL) was added, and the resulting mixture was washed with water (80 mL) and brine (40 mL). The organic layer was dried over magnesium sulfate and then concentrated under reduced pressure. The residue was subjected to chromatography on a silica gel column (hexane/ethyl acetate) to afford N-[[[[(2,6-diisopropylphenyl)amino]carbonyl]amino]sulfonyl]-N-pentyl-N-[[[2'-(triphenylmethyl)tetrazol-5-yl]-1,1'-biphenyl-4-yl]methyl] amine as a colorless amorphous mass (0.32 g).

Yield: 20%.

$^1$H-NMR (CDCl$_3$, ppm):
0.83(t,3H,J=6.5 Hz), 1.09-1.29(m,18H), 3.05-3.29(m,4H), 4.39(s,1H), 4.52(s,1H), 6.87-6.99(m,6H), 7.15-7.51(m,20H), 7.92(dd,1H,J=2.2,5.4 Hz).

N-[[[[(2,6-Diisopropylphenyl)amino]carbonyl]amino]-sulfonyl]-N-pentyl-N-[[[2'-(triphenylmethyl)tetrazol-5-yl]-1,1'-biphenyl-4-yl]methyl]amine (0.32 g) was dissolved in tetrahydrofuran (11 mL). At room temperature, 10% hydrochloric acid was added, and the resulting mixture was stirred. Seventeen hours later, ethyl acetate (60 mL) was added, and the mixture was washed with water (60 mL) and brine (60 mL). The organic layer was dried over anhydrous sodium sulfate and then concentrated under reduced pressure. The residue was subjected to chromatography on a silica gel column (chloroform/methanol) and further, purified by preparative thin-layer chromatography (chloroform/methanol). The thus-obtained crystals were suspended in diisopropyl ether. Crystals were collected by filtration, suspended in diethyl ether, and then collected again by filtration to afford the compound represented by the formula (16)(0.5 g).

$^1$H-NMR (CDCl$_3$, ppm):
0.97(t,3H,J=6.8 Hz), 1.20(s,6H), 1.23(s,6H), 1.40-1.42(m, 4H), 1.76-1.83(m,2H), 3.00-3.16(m,1H), 3.52(t,2H, J=7.0 Hz), 4.52(s,2H), 4.61(s,1H), 7.13-7.31(m,5H), 7.39-7.65(m,6H).

IR (cm$^{-1}$) (KBr):
1517, 1521, 2962.

Test (Evaluation of ACAT Inhibitory Activity)

(1) Preparation of the Enzyme (ACAT)

(1-1) Each rat was reared for about 3 weeks on high-cholesterol feed (solid feed prepared by adding 1% of cholesterol, 0.3% of sodium cholate, 0.1% of propylthiouracil and 3% of lard to a conventional feed MF).

(1-2) The liver of the rat reared in (1-1) was collected and shredded. 10 mM HEPES buffer (pH 7.4) which contained 0.25 M of sucrose and 1 mM of EDTA was added in an amount about three times as much as the weight of the liver to suspend the latter. The liver was then homogenized by a glass-Teflon homogenizer.

(1-3) The homogenized liver was centrifuged for 15 minutes under 22000×g, and the supernatant was collected.

(1-4) The supernatant was centrifuged further for 60 minutes under 100000×g. To the precipitates, 10 mM HEPES buffer (pH 7.4) containing 0.25 M of sucrose and 1 mM of EDTA therein was added in about a half of the volume used in (1-2), and the precipitates were suspended again.

(1-5) The suspension was again centrifuged for 60 minutes under 100000×g, and the resulting precipitates were collected. 10 mM HEPES buffer (pH 7.4) containing 0.25 M of sucrose and 2 mM of DTT therein was added to suspend the precipitates. The suspension was stored at −80° C.

(2) Preparation of Reagents (2-1) Reaction Buffer 0.75 M Phosphate buffer (pH 7.4), 800 µM BSA and 100 mM DTT were mixed together in amounts of 1.0 mL, 0.5 mL and 0.1 mL, respectively, and ultrapure water (3.4 mL) was added.

(2-2) ACAT

A refrigerated sample of the enzyme was diluted with the "reaction buffer" described above to 2.5 mg protein/mL.

(2-3) Test Samples $10^{-3}$ M Solutions of the compounds to be evaluated were prepared with methanol. $3 \times 10^{-4}$ M Solutions were each prepared by adding 50% methanol (700 µL) to the corresponding $10^{-3}$ M solution (300 µL). $10^{-4}$ M Solutions were each prepared by adding 50% methanol (600 µL) to the corresponding $3 \times 10^{-3}$ M solution (300 µL). Up to $10^{-7}$ M solutions (serial 3-fold dilutions), the solutions were prepared by a similar procedure.

(3) Assay Method of ACAT Activity (3-1) ACAT (20 µL), the reaction buffer (20 µL) and desired one (5 µL) of test samples were placed in a 1.5 mL test tube and incubated at 30° C. for 10 minutes (the resulting solution will hereinafter be called "I").

(3-2) Reaction substrate [$^{14}$C]-oleoyl CoA (5 μL) was added into "I", and was allowed to react at 30° C. for 4 minutes.

(3-3) Four minutes later, methanol (250 μL) was added to terminate the reaction, and then, a lipid mixture (40 μL), recovery-percentage-correcting [$^3$H]-cholesteryl oleate (10 μL) and hexane (700 μL) were added into the test tube (this solution will hereinafter be called "II").

(3-4) "II" was stirred in a mixer, and the hexane layer (500 μL) was collected and transferred into another test tube (this solution will hereinafter be called "III").

(3-5) "III" was evaporated to dryness, dissolved in chloroform (10 μL), and then spotted on a TLC plate. At that time, cholesteryl oleate was also spotted.

(3-6) After the spots were dried, they were developed with a 85:15:0.5 mixture of hexane, diethyl ether and acetic acid as a developer solvent, and then stained with iodine. A plate section corresponding to the spot of cholesteryl oleate was cut out and placed in a vial. At the same time, the reaction substrate [$^{14}$C]-oleoyl CoA (5 μL) and the recovery-percentage-correcting [$^3$H]-cholesteryl oleate (10 μL) were spotted on the TLC plate, and similarly, plate sections were cut out and placed in vials, respectively.

(3-7) Subsequently, "Aquazole II" (about 10 mL) was added to the vials. After the vials were allowed to stand for a while, they were measured for [$^{14}$C] and [$^3$H] radioactivities.

Using the radioactivities, the % recovery of [$^{14}$C]-cholesteryl oleate formed by the enzymatic reaction was calculated from the radioactivity of [$^3$H], and from the radioactivity of [$^{14}$C], the yield of cholesteryl oleate was calculated. From the results, a concentration-response curve was prepared, and using the nonlinear least square method, a pIC$_{50}$ value was calculated and was used as an index for ACAT inhibitory activity.

The pIC$_{50}$ values so calculated are shown in Table 1.

TABLE 1

| Compound | PIC$_{50}$ |
|---|---|
| Compound of the formula (4) | 5.72 |
| Compound of the formula (5) | 5.65 |
| Compound of the formula (6) | 5.52 |
| Compound of the formula (7) | 6.23 |
| Compound of the formula (8) | 5.49 |
| Compound of the formula (9) | 5.18 |
| Compound of the formula (10) | 6.57 |
| Compound of the formula (11) | 5.71 |
| Compound of the formula (12) | 6.40 |
| Compound of the formula (13) | 5.39 |
| Compound of the formula (14) | 5.23 |
| Compound of the formula (15) | 5.21 |
| Compound of the formula (16) | 5.51 |

It is understood from the above-described pIC$_{50}$ values that the compounds according to the present invention possess excellent ACAT inhibitory activities.

INDUSTRIAL APPLICABILITY

The invention compounds (1) have excellent ACAT inhibitory activities and are useful as preventives and/or therapeutics for diseases caused by the enhancement of ACAT activity, for example, hypercholesterolemia, atherosclerosis and the like.

What is claimed is:

1. A biphenyl derivative or a salt thereof represented by the following formula (1):

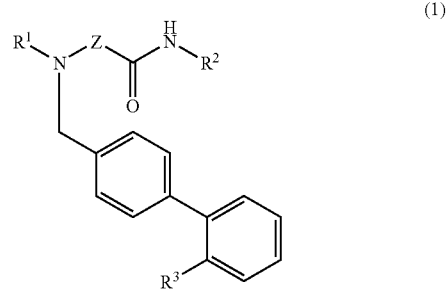

wherein R$^1$ represents a C$_{5-7}$ alkyl group; R$^2$ represents a C$_{6-10}$ aromatic hydrocarbon which may be substituted by 1 to 3 substituents selected from halogen atoms and C$_{1-5}$ alkyl groups, or C$_{3-8}$ cycloalkyl group; R$^3$ represents —NHCOCF$_3$; and Z represents a single bond, a C$_{1-4}$ alkylene group or —SO$_2$NH—.

2. A biphenyl derivative or a salt thereof as defined in claim 1,

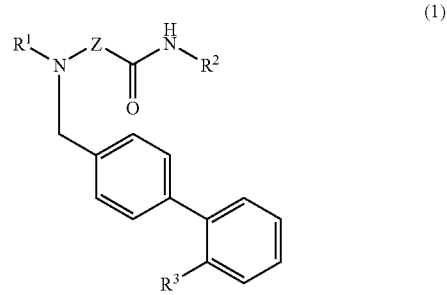

wherein R$^2$ represents a phenyl group which may be substituted by 1 to 3 substituents selected from halogen atoms and C$_{1-5}$ alkyl groups, or C$_{5-7}$ cycloalkyl groups.

3. The biphenyl derivative or salt thereof as claimed in claim 1, wherein R$^1$ is selected from the group consisting of n-pentyl and n-heptyl; R$^2$ is selected from the group consisting of cyclohexyl, 2,6-diisopropylphenyl, 2,4-difluorophenyl, 2,4,6-trimethylphenyl, and 2,4,6-trifluorophenyl.

4. A biphenyl derivative or a salt thereof represented by the following formula (1):

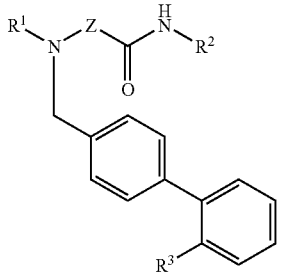

wherein $R^1$ represents a $C_{5-7}$ alkyl group; $R^2$ represents a $C_{3-8}$ cycloalkyl group; $R^3$ represents —NHCOCF$_3$, —NHSO$_2$CF$_3$ or —SO$_2$NHCONHR$^4$ in which $R^4$ represents a $C_{6-10}$ aromatic hydrocarbon group which may be substituted by 1 to 3 substituents selected from halogen atoms and $C_{1-5}$ alkyl groups; and Z represents a single bond, a $C_{1-4}$ alkylene group or —SO$_2$NH—.

5. The biphenyl derivative or salt thereof as claimed in claim 4, wherein $R^1$ is n-heptyl and $R^2$ is cyclohexyl.

6. The biphenyl derivative or salt thereof as claimed in claim 4, wherein $R^1$ is selected from the group consisting of n-pentyl and n-heptyl; $R^2$ is cyclohexyl; and $R^3$ is selected from the group consisting of —NHSO$_2$CF$_3$ and —NHCOCF$_3$.

7. A biphenyl derivative or a salt thereof represented by the following formula (1):

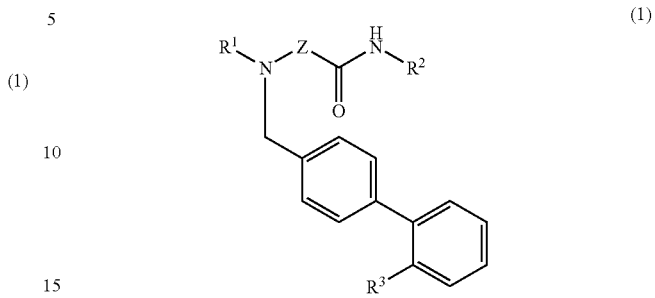

wherein $R^1$ represents a $C_{5-7}$ alkyl group; $R^2$ represents a $C_{6-10}$ aromatic hydrocarbon which may be substituted by 1 to 3 substituents selected from halogen atoms and $C_{1-5}$ alkyl groups, or $C_{3-8}$ cycloalkyl group; $R^3$ represents —NHCOCF$_3$, —NHSO$_2$CF$_3$ or —SO$_2$NHCONHR$^4$ in which $R^4$ represents a $C_{6-10}$ aromatic hydrocarbon group which may be substituted by 1 to 3 substituents selected from halogen atoms and $C_{1-5}$ alkyl groups; and Z represents a $C_{1-4}$ alkylene group or —SO$_2$NH—.

8. A medicinal composition comprising the biphenyl derivative or salt thereof as claimed in claims 1, 2, 4, or 7, and a pharmacologically acceptable carrier.

9. The biphenyl derivative or salt thereof as claimed in claim 7, wherein $R^1$ is selected from the group consisting of n-pentyl and n-heptyl; $R^2$ is selected from the group consisting of cyclohexyl, 2,6-diisopropylphenyl, 2,4-difluorophenyl, 2,4,6-trimethylphenyl, and 2,4,6-trifluorophenyl; and $R^3$ is selected from the group consisting of —NHSO$_2$CF$_3$ and —NHCOCF$_3$.

* * * * *